United States Patent [19]

Mills

[11] Patent Number: 4,784,155

[45] Date of Patent: Nov. 15, 1988

[54] DEVICE FOR AUTOMATED DETECTION OF ESTRUS IN FARM ANIMALS

[75] Inventor: Perry A. Mills, Roseville, Minn.

[73] Assignee: Data Sciences, Inc., Roseville, Minn.

[21] Appl. No.: 74,930

[22] Filed: Jul. 17, 1987

[51] Int. Cl.$^4$ .............................................. A61B 5/05
[52] U.S. Cl. .................................... 128/734; 128/738; 128/903
[58] Field of Search ................ 128/738, 734, 903, 693

[56] References Cited

U.S. PATENT DOCUMENTS

| | | | |
|---|---|---|---|
| 3,297,020 | 1/1967 | Mathiesen | 128/738 |
| 3,566,233 | 2/1971 | Kahn et al. | 128/734 X |
| 3,730,171 | 5/1973 | Namon | 128/734 X |
| 3,844,276 | 10/1974 | McDougall | 128/734 X |
| 3,851,641 | 12/1974 | Toole et al. | 128/734 X |
| 4,008,712 | 2/1977 | Nyboer | 128/734 |
| 4,224,949 | 9/1980 | Scott et al. | 128/738 X |
| 4,411,274 | 10/1983 | Wright | 128/903 X |
| 4,498,481 | 2/1985 | Lemke | 128/734 |
| 4,630,615 | 12/1986 | Yomtov | 128/734 |
| 4,685,471 | 8/1987 | Regas et al. | 128/734 |

FOREIGN PATENT DOCUMENTS 0221635 5/1985 Fed. Rep. of Germany ...... 128/738

Primary Examiner—Kyle L. Howell
Assistant Examiner—Angela D. Sykes
Attorney, Agent, or Firm—Kinney & Lange

[57] ABSTRACT

A telemetry system includes a transmitter, which is either placed in the vagina or is implanted in the vulvular or vaginal tissue, and a receiver. The transmitter is capable of measuring physiological parameters which are indicative or predictive of the occurrence of estrus. These parameters may include but are not limited to tissue impedance, temperature and activity of the animal. This provides a pulsed method of measuring impedance of vulvular or vaginal tissue which enhances the marketability of such a device by reducing its size, weight and complexity without sacrificing accuracy or reliability. Data telemetered from this device is preferably collected by a computer and automatically analyzed to provide a report to the farm manager as to which animals are in estrus or are expected to be in estrus at a given time.

13 Claims, 3 Drawing Sheets

DEVICE FOR AUTOMATED DETECTION OF ESTRUS IN FARM ANIMALS

BACKGROUND OF THE INVENTION

1. Field of the Invention

The present invention relates to a device for monitoring farm animals for the purpose of detecting estrus.

2. Description of the Prior Art

For economic reasons and improved genetic traits, many farm animals are bred using artificial insemination. When using artificial insemination, a method of estrus detection is employed to judge the appropriate time for insemination. Failure to properly detect estrus results in failure to conceive. In the United States, the most pressing need for an automated system for detecting estrus is in the dairy industry. Failure to conceive at the desired time results in loss of milk production, increased culling of producing animals, reduced number of calves which can be sold due to the need to replace culled animals, and other factors which have a negative economic impact. Estimates place the annual per head loss for the average dairy herd at $150.00 to $300.00 per animal.

The most common method of estrus detection employed by the United States dairy industry is to visually observe the behavior and condition of herd animals at feeding and milking times. A number of factors have been documented (see U.S. Pat. No. 3,844,273, and *The Veterinary Record*, July 15, 1972, pages 50–58) which can be observed visually to detect estrus in dairy animals.

Several techniques have been proposed in either the scientific literature or in patents to either automate the process of estrus detection or improve its accuracy beyond visual observation of the herd. These techniques include the use of heat mount detectors (see Kaymar, Inc. product literature, Steamboat Springs, Colo.), the use of pedometers for the measurement of movement activity (see U.S. Pat. No. 4,247,758), the use of video cameras and recorders to provide twenty-four hour observations of behavior (see *Canadian Journal of Animal Science*, June 1976, Volume 56, pages 291–298), the use of probes to measure vaginal impedance (see Animal Tek product literature, Boulder, Colorado), measurement of body temperature, and the measurement of milk or blood progesterone.

Heat mount detectors involve the use of a patch which is attached to the back of the animal near the tail. When an animal is in estrus, she will stand to be ridden by other animals. When an animal is ridden by another animal, a pouch located in the patch which is filled with bright colored ink bursts, indicating that the animal was receptive to being mounted and is probably in estrus. Although heat mount detectors have been shown to be effective as an aid for detecting estrus, their major limitation is that they fall off the animal too frequently and do not lend themselves to automation.

Pedometers have also been shown to provide a significant improvement over the norm in their ability to determine if an animal is in estrus, although thorough testing has not yet been performed. The obvious limitation of this technology is that a large percentage of dairy herds in the northern United States are stanchioned most of the time, limiting the degree of changes in activity which could be perceived.

Video cameras and recorders have also been shown to be effective, but they require considerable labor to review recordings and a sizable capital investment.

Measurement of body temperature has been tried as a means of estrus detection. However, changes in environmental temperature often mask changes induced by estrus and measurement of temperature by itself is considered to provide a poor indicator of estrus.

Measurement of progesterone levels is a very effective way of detecting estrus. However, the cost of such assays makes common use of this method prohibitive.

Research indicates that measurement of impedance may provide an accurate and reliable means of detecting estrus. Combining measurement of impedance with other parameters such as temperature and movement activity would very likely improve the accuracy and reliability of estrus detection.

In addition to the ability to detect estrus, research indicates that measurement of impedance may have the additional benefits of being able to detect pregnancy and the approach of parturition, and may also provide a screening tool of genital disorders.

The use of impedance for detecting estrus was first reported by Aizinbudas and Dovilitis in the journal *Zhivotnovodstvo* 11:68–70 in 1962. Published studies in which vaginal impedance has been measured have done so by measuring the tissue impedance when stimulated by a sinusoidal waveform of a specific frequency.

Animark of Boulder, Colorado and Animal Tek each manufacture a probe capable of measuring impedance which can be temporarily inserted into the vagina. Field trials of these devices indicate that they are relatively ineffective at detecting estrus. Frequent insertions are required in order to detect estrus, resulting in vaginal inflammation and occasionally, infection.

SUMMARY OF THE INVENTION

The present invention is a system and method for measuring tissue or intravaginal impedance of female farm animals which includes a transmitter for transmitting sensed impedance which may be implanted in the vulvular or vaginal tissue, or inserted into the vagina. The transmitter includes a housing, a pair of electrodes which make contact with the tissue and between which impedance is measured, and a battery to power the circuitry. When implanted or placed in the vagina, the transmitter transmits signals which indicates the impedance between the electrodes on the outer housing of the transmitter.

With the present invention, a method of measuring impedance is presented which is simple to implement, requires a minimal number of components and minimizes required battery current, resulting in a device which is less expensive to manufacture and of smaller size and weight.

In the preferred embodiment of the present invention, the transmitter circuit uses the value of tissue impedance between two electrodes implanted in living tissue to determine the period between bursts of radio frequency (RF) energy that it transmits. An external receiver detects these RF bursts and sends the resulting signal to a computer. The computer creates a digital word representing the period between RF pulses and stores it in a file for later retrieval and analysis.

DETAILED DESCRIPTION OF THE PREFERRED EMBODIMENTS

Figure 1:
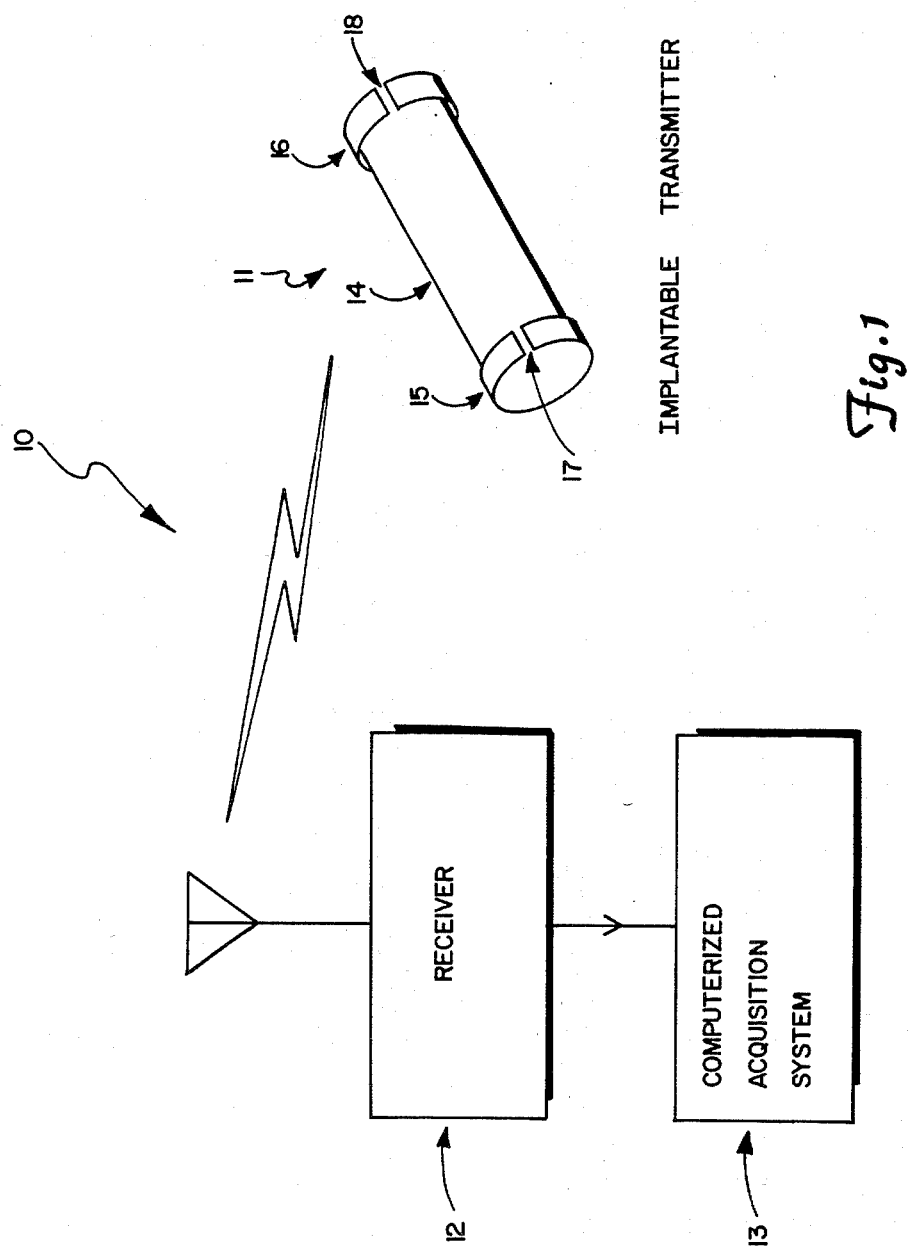
FIG. 1 is a block diagram of the telemetry system of the present invention.

As shown in FIG. 1, telemetry system 10 of the present invention includes implantable, battery-powered transmitter 11, receiver 12, and computerized acquisition system 13. Transmitter 11 has a housing 14 to which a pair of electrodes 15 and 16 are mounted at either end. Electrodes 15 and 16 contact the tissue of which impedance is measured. Transmitter 11 measures the impedance of the tissue in contact with electrodes 15 and 16 and transmits this information to receiver 12. Receiver 112 reconstructs the transmitted signal and relays it to computerized acquisition system 13, where the information is decoded, stored, displayed and analyzed for the purpose of automatic detection of estrus.

Sensing electrodes 15 and 16 are constructed of a narrow ring of noble metal, and employ gaps 17 and 18 which provide a discontinuity to transmitted RF energy, thereby providing for more efficient RF transmission.

Transmitter 11 produces the transmitted RF signal in the form of a pulse train of RF bursts. The period P (see FIG. 3) between two pulses is determined by the value of tissue resistance (Rs) at a time immediately following the first pulse. Rs is the real series component (resistance 24) of the complex impedance between the pair of ring electrodes 15 and 16 imbedded in living tissue. The relationship between period P and Rs, for Rs greater than zero, is $P = K(Rs - Ro)$. K is a constant and Ro is the minimum value of Rs that can be measured before the period P goes to zero.

Figure 2:
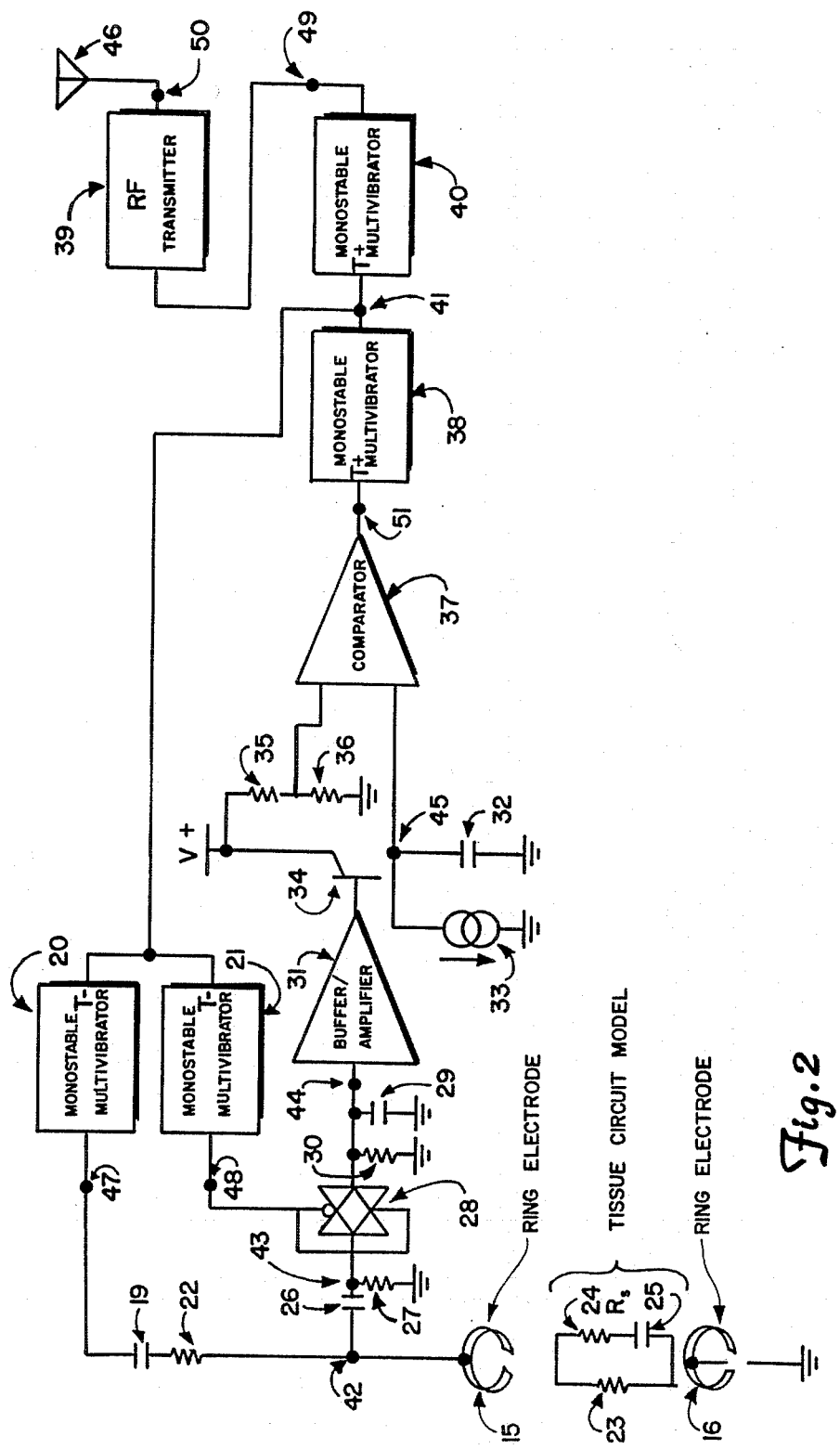
FIG. 2 is an electrical schematic diagram of the transmitter of the telemetry system of FIG. 1.
Figure 3:
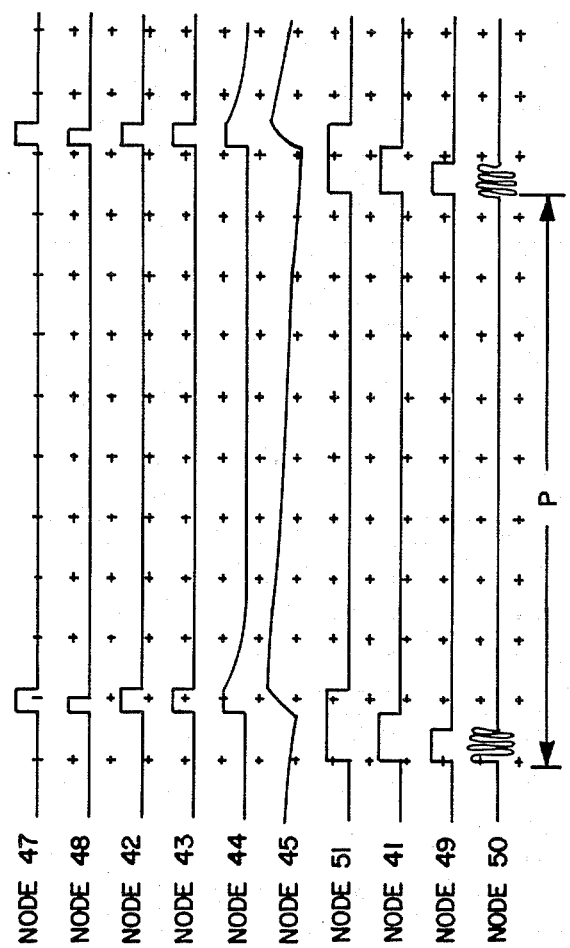
FIG. 3 shows waveforms produced at various nodes of the transmitter of FIG. 2.

Implantable transmitter 11 functions in the following manner, as illustrated in the schematic diagram of FIG. 2 and the waveforms of FIG. 3. A negative-going voltage transition at circuit node 41 of FIG. 2 triggers monostable multivibrators 20 and 21. Monostable 20 creates a positive pulse which drives capacitor 19 and resistor 22. Capacitor 19 is large in value and functions to inhibit the flow of direct current through electrodes 15 and 16, thus preventing electrode erosion due to electrolysis. The voltage pulse across resistor 22 results in a current pulse which flows through electrode 15, the tissue (represented in FIG. 2 by circuit model consisting of resistors 23 and 24 capacitor 25) and electrode 16 to ground reference. This current pulse which flows through the tissue generates a voltage pulse at node 42, the amplitude of which is primarily determined by the value Rs of resistor 24 of the tissue circuit model. The current pulse is short enough that the resulting voltage generated across tissue circuit model capacitor 25 is insignificant due to its large capacitance. The effect of tissue circuit model resistor 23 is also insignificant since its value is normally very large compared to tissue circuit model resistor 24.

Capacitor 26 and resistor 27 a.c. couple the voltage pulse at node 42 to node 43. This signal must be a.c. coupled since electrodes 15 and 16 often develop an offset voltage which must be eliminated to obtain an accurate impedance measurement. Transmission gate 28 is controlled by a pulse from monostable 21 during which time it connects node 43 to node 44. Since the value of capacitor 26 is large relative to capacitor 29, the voltage present at node 43 prior to activation of transmission gate 28 appears at node 44 following activation of transmission gate 28. Since the pulse generated by monostable 21 is shorter than that generated by monostable 20, transmission gate 28 turns off before the end of the voltage pulse at node 43, leaving the voltage present at node 43 stored on capacitor 29. High impedance buffer/amplifier 31 amplifies the voltage on capacitor 29 resulting in a proportional voltage on capacitor 32. Storing the voltage present at node 43 on capacitor 29 allows buffer/amplifier 31 to have a very low slew rate and operate at very low current, thereby making possible an extended lifetime and/or a smaller package size for transmitter 11 due to reduced current demand on the battery.

The voltage on capacitor 32 is discharged slowly by current sink 33. After capacitor 32 is initially charged buffer/amplifier 31 and transistor 34 have no effect since capacitor 29 is discharged by resistor 30 much more rapidly than capacitor 32 is discharged by current sink 33. The higher discharge rate of capacitor 29 relative to capacitor 32 results in the output of buffer/amplifier 31 going to a lower voltage than node 45, leaving the base-emitter junction of transistor 34 reverse biased. When capacitor 32 discharges to the threshold voltage present at the positive input of comparator 37, the output of comparator 37 switches to a high voltage. Since capacitor 32 was initially charged to a voltage proportional to the resistance value Rs of tissue circuit model resistor 24, the time from the initial charging of capacitor 32 to the change in state of comparator 37 is determined by the value Rs of tissue circuit model resistor 24. When comparator 37 changes state, the positive going voltage at its output triggers monostable multivibrator 38 generating a positive pulse at its output. The leading (positive-going) edge of this pulse triggers monostable multivibrator 40, generating a positive pulse at its output. This pulse drives an RF transmitter section 39 which delivers RF energy to antenna 46 during the pulse. The lagging (negative-going) edge of the pulse at node 41 triggers monostables 20 and 21 to start a new impedance measuring cycle. Monostables 20 and 21 are triggered on the lagging edge of the pulse at node 41 and monostable 39 on the leading edge in order to make the time when impedance is measured and the time when RF energy is transmitted mutually exclusive. Failure to arrange the timing in this fashion would result in the presence of the RF energy proximal to the impedance measuring circuitry and subsequent distortion of the measurement.

This implementation of the present invention can be modified to measure both the real (tissue circuit model resistor 24) and imaginary (tissue circuit model capacitor 25) components of tissue impedance. The ability to do so provides the potential advantage of measuring additional information concerning tissue impedance which may allow for a more reliable and sensitive means of determining or predicting estrus. In order to measure both real and imaginary impedance, the widths of the pulses generated by monostables 20 and 21 must be modified. The pulse widths of monostables 20 and 21 described above are chosen to be short enough such that the charging of tissue circuit model capacitor 25 is negligible during the pulse, and therefore the voltage which is measured at node 43 is primarily determined by tissue circuit model resistor 24. Extending the width of the pulses generated by monostables 20 and 21 to approximately ten times (e.g. 15 and 10 microseconds rather than about 1.5 and 1.0 microseconds, respectively) allows tissue circuit model capacitor 25 enough time to charge such that an incremental voltage increase appears at node 43, beyond that which results from tissue circuit model resistor 24 and which is inversely proportional to the value of capacitor 25. The period between transmitted RF pulses then indicates the sum of the impedance due to resistor 24 and capacitor 25.

Another embodiment of this invention allows independent measurement of tissue circuit model components, resistor 24 and capacitor 25. The voltage at node 43 is measured both following a short excitation pulse and a long excitation pulse, and signals are transmitted which are proportional to each. An independent measurement of the value of tissue circuit model capacitor 25 can be obtained by subtracting the voltage measured at node 43 following the short excitation pulse from that measured following the longer excitation pulse. The resulting difference is indicative of the value of tissue circuit model capacitor 25.

One implementation of this concept alternately uses the signal derived from the short and long excitation pulses to determine the time between RF pulses at the transmitter output. A comparison of the two pulse intervals yields a value for tissue circuit model capacitor 25. The excitation and gating pulses produced by monostables 20 and 21 switch alternately between short and long pulse widths.

Another enhancement of the present invention uses a microcomputer within the transmitter to control the sampling of the physiological measurements. The microcomputer also stores the information at regular intervals, and then transfers the information to receiver 12 of FIG. 1 and computerized data acquisition, display and analysis system (CDADA) 13 upon command by an interrogator. In this embodiment, CDADA 13 controls a means for requesting that the microcomputer located within transmitter 11 transmit collected data to the receiver. In order to limit the power requirements of transmitter 11, interrogation hardware is located at locations which would be commonly visited by the animals (such as milking areas, watering tanks or feed dispensers) so that interrogation can be performed at short range. The computer acquisition system 13 positively identifies transmitter 11 and causes it to transmit collected data to receiver 12 which in turn reconstructs the transmitted signal and transfers of the data to CDADA 13.

The use of a pulse (as compared to a sine wave used in the prior art as a means of stimulating the tissue for the purpose of measuring impedance) provides an approach which requires less current drain. Since this approach requires less current drain, a smaller battery will result in an equivalent lifetime, all other factors being equal. The smaller battery in turn results in a smaller package size, providing a significant advantage for a battery-powered device which must be implanted in the vaginal or vulvular tissue.

Although the present invention has been described with reference to preferred embodiments, workers skilled in the art will recognize that changes may be made in form and detail without departing from the spirit and scope of the invention.

What is claimed is:

1. A transmitter for transmitting an output signal which is a function of resistive and reactive components of impedance of tissue in a reproductive system of a female animal, the transmitter comprising:

first and second electrode means for making electrical contact with the tissue;

means for supplying pulses of first and second different pulse widths to the first and second electrode means at first and second time intervals which are a function of the impedance between the first and second electrode means, so that differences in the first and second time intervals are a function of the reactive component of the impedance of the tissue, and duration of the first time intervals is a function of the resistive component; and output means for producing the output signal with a characteristic which is a function of the first and second time intervals.

2. The transmitter of claim 1 and further comprising:

housing means for containing the means for supplying pulses and the output means.

3. The transmitter of claim 2 wherein the first and second electrode means are supported on an exterior surface of the housing means adjacent first and second ends, respectively, of the housing means.

4. The transmitter of claim 3 wherein the housing means is generally cylindrical, and wherein the first and second electrode means comprise first and second conductive, partial circumferential rings adjacent the first and second ends of the housing means, respectively.

5. The transmitter of claim 1 wherein the output means comprises RF transmitter means for producing the output signal as a burst of RF energy each time a pulse is supplied by the pulse generator means.

6. The transmitter of claim 1 wherein the means for supplying pulses comprises:

means for supplying current pulses to the first and second electrode means;

means for deriving first signals from the first and second electrode means which are produced in response to the current pulses and are a function of the resistive and reactive components of impedance between the first and second electrode means;

means for comparing the first signals with a second reference signal to produce a third signal which has first and second states; and means for triggering the means for supplying current pulses in response to a transition of the third signal from the second to the first state.

7. The transmitter of claim 6 wherein the output means comprises:

RF transmitter means for producing the output signal as a burst of RF energy; and means for triggering the RF transmitter means in response to a transition of the third signal from the first to the second state.

8. The transmitter of claim 7 wherein the burst of RF energy produced by the RF transmitter means has a time duration which is less than a time period during which the third signal is in the second state.

9. The transmitter of claim 7 and further comprising:

means for separating in time the producing of the burst of RF energy and the deriving of the first signal such that the burst of RF energy does not adversely affect measurement of the impedance.

10. The transmitter of claim 6 wherein the means for supplying current pulses alternately produces the current pulses with first and second, different pulse widths.

11. A transmitter for transmitting an output signal which is a function of resistive and reactive components of impedance of tissue in a reproductive system of a female animal, the transmitter comprising:

first and second electrode means for making electrical contact with the tissue;

means for supplying first and second current pulses of first and second different pulse widths to the first and second electrode means;

means for sampling a holding a first voltage and a second voltage produced across the first and second electrode means as a result of the first and second current pulses, respectively;

means for converting the first and second voltages to first and second time periods; and means for producing an output signal which is a function of the first and second time periods.

12. A transmitter for transmitting an output signal which is a function of resistive and reactive components of impedance of tissue in a reproductive system of a female animal, the transmitter comprising:

first and second electrode means for making electrical contact with the tissue;

means for supplying first and second current pulses of first and second pulse widths to the first and second electrode means, the first pulse width being short enough that a voltage produced between the electrode means in response to the first current pulse is a function of the resistive component only, and the second pulse width is long enough that a voltage produced between the electrode means in response to the second current pulse is a function to both the resistive component and the reactive component and output means for producing the output signal as a function of the voltages produced in response to the first and second current pulses.

13. A transmitter for transmitting an output signal which is a function of resistive and reactive impedance of tissue in a reproductive system of a female animal, the transmitter comprising:

first and second electrode means for making electrical contact with the tissue;

means connected to the first and second electrode means for providing a first signal which is a function of measured resistive impedance between the first and second electrode means;

means connected to the first and second electrode means for providing a second signal which is a function of measured reactive impedance between the first and second electrode means; and output means responsive to the first and second signals for transmitting an output signal from which separate values of measured resistive and reactive impedance can be derived.

* * * * *

UNITED STATES PATENT AND TRADEMARK OFFICE
CERTIFICATE OF CORRECTION

PATENT NO. : 4,784,155

DATED : November 15, 1988

INVENTOR(S) : Perry A. Mills

It is certified that error appears in the above-identified patent and that said Letters Patent is hereby corrected as shown below:

Column 7, line 8, after "sampling", delete "a" (second occurence) and insert --and--.

Signed and Sealed this

Twenty-eighth Day of March, 1989

Attest:

DONALD J. QUIGG

Attesting Officer

Commissioner of Patents and Trademarks